US008920023B2

(12) United States Patent
Sloan

(10) Patent No.: US 8,920,023 B2
(45) Date of Patent: *Dec. 30, 2014

(54) CRYOGENIC NON DESTRUCTIVE TESTING (NDT) AND MATERIAL TREATMENT

(76) Inventor: Victor Sloan, Palo Alto, CA (US)

(*) Notice: Subject to any disclaimer, the term of this patent is extended or adjusted under 35 U.S.C. 154(b) by 359 days.

This patent is subject to a terminal disclaimer.

(21) Appl. No.: 13/095,501

(22) Filed: Apr. 27, 2011

(65) Prior Publication Data

US 2012/0034044 A1 Feb. 9, 2012

Related U.S. Application Data

(60) Provisional application No. 61/371,627, filed on Aug. 6, 2010, provisional application No. 61/388,275, filed on Sep. 30, 2010.

(51) Int. Cl.
| | |
|---|---|
| *G01K 3/00* | (2006.01) |
| *G01N 25/72* | (2006.01) |
| *G01N 29/14* | (2006.01) |
| *G01N 25/04* | (2006.01) |
| *G01N 29/11* | (2006.01) |
| *G01N 29/30* | (2006.01) |
| *G01N 29/44* | (2006.01) |
| *G01N 29/46* | (2006.01) |

(52) U.S. Cl.
CPC ............... *G01N 29/14* (2013.01); *G01N 25/04* (2013.01); *G01N 29/11* (2013.01); *G01N 29/30* (2013.01); *G01N 29/4436* (2013.01); *G01N 29/46* (2013.01); *G01N 2291/0251* (2013.01); *G01N 2291/0289* (2013.01); *G01N 2291/044* (2013.01)
USPC .............................................. 374/5; 374/102

(58) Field of Classification Search
USPC ................... 374/E3.004, E7.039, 102, 163, 5
See application file for complete search history.

(56) References Cited

U.S. PATENT DOCUMENTS 2,778,755 A * 1/1957 Brown et al. ................. 148/658
4,140,021 A * 2/1979 Nomura et al. ................. 73/587

(Continued)

OTHER PUBLICATIONS

Purtsher P.T. , Krauss G., and Matkick D.K. "Temperature-Induced Transition in Ductile Fracture Appearance of a Nitrogen-Strengthened Austenitic Stainless Steel", Metallurgical Transactions, vol. 24A. Nov. 1993, p. 2521-2529.*

(Continued)

*Primary Examiner* — Lisa Caputo
*Assistant Examiner* — Nasir U Ahmed
(74) *Attorney, Agent, or Firm* — Duane Morris LLP; Patrick C. Muldoon

(57) ABSTRACT

A non-destructive test using cryogenic temperatures is capable of detecting defects in materials that result from residual stress from manufacturing and from retained austenite. The subject materials or parts that are subjected to cryogenic temperatures approaching and below~–300° F., –184° C., 89° K, thereby causing permanent deformations or characteristic changes in the material if excessive residual stress, retained austenite or discontinuities exist. To determine the extent of changes, a first metric of the subject material is determined, the material is then subjected to cryogenic cooling thereby triggering any deformation or characteristic changes. Subsequent to the cryogenic cooling, the subject material may be returned to a second temperature whereby a second metric representing based on the same characteristic of the subject material is determined The comparison of the first and second metrics reveals the deformation or change resultant from the defect. In addition characteristic changes in the subject material during cryogenic cooling may be use to detect the phase transition of the retained austenite to martensite.

42 Claims, 11 Drawing Sheets

(56) References Cited

U.S. PATENT DOCUMENTS

| | | | |
|---|---|---|---|
| 4,309,903 A * | 1/1982 | Ono | 73/587 |
| 4,463,733 A * | 8/1984 | Tsai | 123/501 |
| 4,523,965 A * | 6/1985 | Lyman | 148/578 |
| 5,209,568 A * | 5/1993 | Buffard et al. | 374/49 |
| 5,218,296 A * | 6/1993 | Shinde et al. | 324/239 |
| 5,695,050 A * | 12/1997 | Weaver | 206/150 |
| 5,885,370 A * | 3/1999 | Shimotomai et al. | 148/108 |
| 5,920,014 A * | 7/1999 | Waschkies | 73/597 |
| 6,565,678 B2 * | 5/2003 | Fairchild et al. | 148/336 |
| 6,848,390 B2 * | 2/2005 | Akers et al. | 116/216 |
| 7,114,340 B2 * | 10/2006 | Pecharsky et al. | 62/3.1 |
| 7,161,124 B2 * | 1/2007 | Kisner et al. | 219/635 |
| 7,190,161 B2 * | 3/2007 | Bomya | 324/228 |
| 7,275,442 B2 * | 10/2007 | Bentzel | 73/643 |
| 7,500,953 B2 * | 3/2009 | Oraevsky et al. | 600/458 |
| 7,516,022 B2 * | 4/2009 | Lee et al. | 702/39 |
| 7,546,873 B2 * | 6/2009 | Kim et al. | 166/245 |
| 7,563,021 B2 * | 7/2009 | Ichihara et al. | 374/46 |
| 7,636,817 B1 * | 12/2009 | Pritchard | 711/149 |
| 2002/0020470 A1 * | 2/2002 | Okumura et al. | 148/108 |
| 2007/0068605 A1 * | 3/2007 | Statnikov | 148/558 |
| 2007/0267351 A1 * | 11/2007 | Roach et al. | 210/695 |
| 2007/0276638 A1 * | 11/2007 | Borchers et al. | 703/6 |
| 2008/0022773 A1 * | 1/2008 | McKenna et al. | 73/597 |

OTHER PUBLICATIONS

P.T. Purtscher, G. Krauss, and D.K. Matlock, "Temperature-Induced Transition in Ductile Fracture Appearance of a Nitrogen-Strengthened Austenitic Stainless Steel", Metallurgical Transactions, vol. 24A, Nov. 1993, pp. 2521-2529.*

B. I. Voronenko, "Acoustic emission during phase transformations in alloys", Metal Science and Heat Treatment, vol. 24, Issue 8, pp. 545-553, Aug. 1982.*

Wei Wang, Wei Yan, Ke Yang, Yiyin Shan, and Zhouhua Jiang, "Temperature Dependence of Tensile Behaviors of Nitrogen-Alloyed Austenitic Stainless Steels", Journal of Materials Engineering and Performance, vol. 19(8), p. 1214-1219, Nov. 2010.*

"Agilent Spectrum Analysis Basics, application Note 150", Apr. 27, 2004.*

Michael B. Prime, "Cross-Sectional Mapping of Residual Stresses by Measuring the Surface Contour After a Cut," Journal of Engineering Materials and Technology, Apr. 2001, pp. 162-168, vol. 123.

* cited by examiner

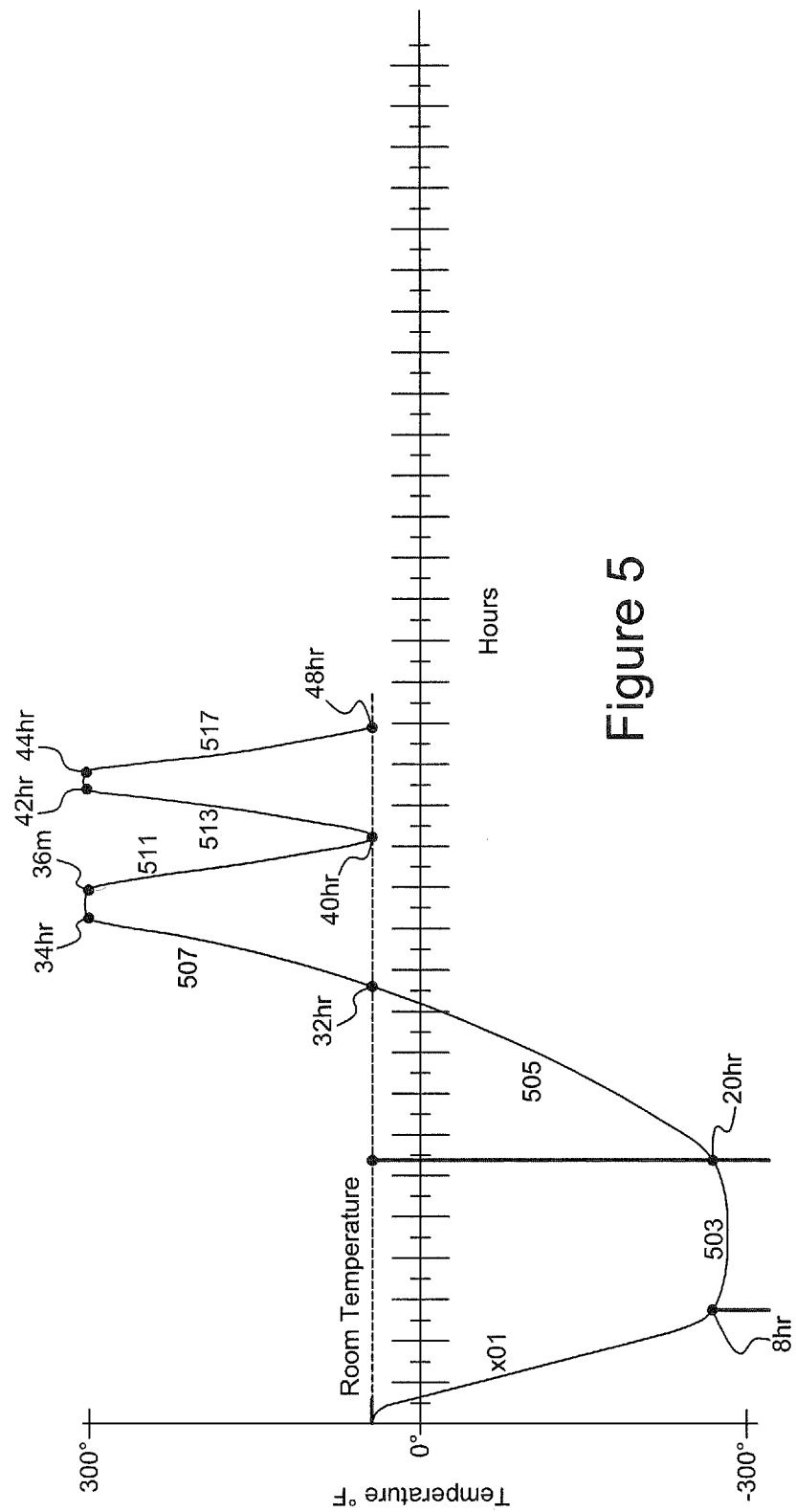

CRYOGENIC NON DESTRUCTIVE TESTING (NDT) AND MATERIAL TREATMENT

CROSS REFERENCES

This application is a non-provisional application claiming priority of co-pending provisional applications: Application No. 61/371,627 entitled CRYOGENIC NON-DESTRUCTIVE TESTING AND MATERIAL TESTING filed Aug. 6, 2010; Application No. 61/388,275 entitled CRYOGENIC NONDESTRUCTIVE TESTING filed Sep. 30, 2010. This application is also co-pending and concurrently filed with non-provisional application entitled CRYOGENIC TRANSITION DETECTION. The entirety of each referenced provisional and non provisional application is incorporated herein by reference.

BACKGROUND

During the manufacture of machine parts and metallic components, including but not limited to engine power transmission and geared elements, testing of the constituent parts, or representative samples there from, is an essential method for quality control, and this is of particular importance in certain fields, such as vehicles, turbine, aviation and aerospace applications, in which component failure could have catastrophic results.

For example, aircraft engines are quite different from most automobile engines as they rely entirely on available air-cooling to control engine oil and part temperatures. The engine is exposed to significant changes in temperature as a result of changing airflow and rapid expansion and cooling of the engine parts occur. This can cause premature engine parts failure, reduction of power and oil leaks to occur.

On most automotive engines manufactured today, the engine temperature is cooled by water circulation and is automatically temperature controlled using a thermostat thus eliminating the vast engine temperature changes that occur in air-cooled aircraft engines.

Because aircraft engines are subjected to this rapid expansion and contraction of engine parts any residual stress that is in the engine parts can significantly affect the life of an engine. Residual stress occurs in parts at rest, and may be a by-product of manufacturing processes and cyclic use.

The need for such quality testing in which metallic component failure could have a catastrophic result is often not well or completely met in the metallic context by presently available testing methods. First, destructive testing methods are limited because of the various means in which such part destruction results in distortions which mask or obliterate the forensic value of the particular component under such examination.

Currently there are many forms of Non Destructive Testing Processes (NDT) for metallic materials that include but are not limited to examples as follows: X-ray diffraction (xrd), Radiography (rt), Convergent beam electron diffraction (cbed), Transmission electron microscopy (tem), Neutron diffraction, Synchrotron hard x-ray, Eddy current (et), Magnetoelastic instrumentation barkhausen noise (bn), Ultrasonic resonant analysis, Magnetoacoustic, Ultrasonic, Thermoelastic infared, Photoelastic, Electronic speckle pattern interferometry, Magnetic particle, Magnaflux quasar process compensated resonant inspection (peri), and Acoustic resonance. Other forms of non destructive testing have limitations in their practical value due to, for one example, refraction issues in the x-ray context.

The present subject matter may augment, incorporate, modify or substitute for the above identified testing procedures.

Of particular importance is the detection of residual stress in a part or product. Residual stress is stress present in a body that is free of external forces or temperature gradients. Residual stress can be induced through manufacturing processes such as heat treating, machining, shot peening, forming, grinding, casting and other procedures that have been applied to a material.

Under typical parts, manufacturing conditions, temperature gradients can produce non-uniform dimensional and volume changes. When metal castings cool and solidify, compressive stresses develop in lower-volume areas, which cool first, and tensile stresses develop in areas of greater volume, which are last to cool. Shear stresses can develop between the different volume areas. This can happen even in large castings and machine parts of relatively uniform thickness. The surface cools first and the core last. In such cases, stresses develop as a result of the phase (volume) change between those layers that transform first and the center portion, which transforms last.

When both volume and phase changes occur in metal parts of uneven cross section, normal contractions due to cooling are opposed by transformation expansion. The resulting residual stresses will remain until a means of relief is applied. This type of stress develops most frequently in steels during a quenching process frequently used in parts manufacturing. As a result, the surface becomes harder before the interior does. Although the inner materials can be strained to match this surface change, subsequent interior expansions place the surface of the metal under tension when the inner material transforms. Cracks in high-carbon steels can arise from such stresses and cause pre-mature parts failure when under load stress.

Grinding operations, when parts are machined, may cause residual stresses in parts such as crankshafts, camshafts and gears. During an initial grinding process the part being ground will have an elevated surface temperature as a result of the grinding wheel contact. The surface of the part being ground becomes heated while the surrounding metal constrains expansion around the grinding area. As the machined metal cools after grinding it can leave a tensile residual stress on the surface. At a later point in time as the part is subjected to operational stresses from normal engine operation, surface cracks can develop causing premature parts failure.

One example of destructive testing for residual stress is presented in "Cross-Sectional Mapping of Residual Stresses by Measuring the Surface Contour After a Cut" M. B. Prime, Journal of Engineering Materials and Technology. Volume 123, April 2001, pp. 162-168, the entirety of which is incorporated herein by reference. In Prime and other methods, residual stresses may be determined from deformation measured after material is removed and destroyed. These methods have the disadvantages of destructive testing as described previously.

One common mechanism, in addition to manufacturing induced stress, which introduces residual stress is the transformation or incomplete transformation of austenite to martensite in the manufacture of steel parts.

Material Structure Transformation

Hardening of steels requires that the material be heated to a high temperature followed by a quenching and tempering process. During the heating cycle, the room temperature phase is transformed into a face-centered cubic structure known as Austenite. During quenching, the Austenite will then transform into fresh martensite, which is a very hard, but brittle phase. Thus, the tempering process is almost always undertaken to reduce the brittleness of the steel at the expense of a slight loss in hardness. In real life, however, the heat treatment process is not as ideal as this. Often, some of the Austenite will be retained after quenching and tempering, which can lead to a degradation in the materials performance. This is due to the fact that the retained Austenite can be transformed into fresh, untempered martensite by applied stresses while in use. Also, the transformation of the retained Austenite will cause a dimensional instability in the part, leading to quality control problems.

Retained austenite can be present in materials after various manufacturing methods have been completed. It is usually the result of uneven or inadequate quenching in hardened steels or cast irons. The hardening process of steel involves heating the component up to a temperature where the atoms arrange themselves into a face centered cubic crystal structure as shown in FIG. 1. If this structure is cooled quickly enough, it transforms by a diffusion less shear transformation into a body centered crystal structure called Martensite as shown in FIG. 2.

Martensite is an acicular microstructure that is very brittle and highly stressed in its primary phase. This brittleness is removed by proper tempering. Tempering is the reheating of hardened steel or cast iron to some temperature below the eutectic temperature for the purpose of decreasing hardness and increasing toughness. Martensite forms during quenching, when the face centered cubic lattice of austenite is distorted into the body centered tetragonal structure without the loss of its contained carbon atoms into cementite and ferrite. Instead, the carbon is retained in the iron crystal structure, which is stretched slightly so that it is no longer cubic. Martensite is more or less ferrite supersaturated with carbon.

The problems with retained austenite are many. Hardness of a metal with significant retained austenite will vary over a wide range. The austenitic structure is about 4% smaller than the martensitic structure, so the conversion of retained austenite may create stresses and warping due to its change in density and volume, all of which may result in a premature failure or degradation of performance of the material.

In order to provide for non-destructive testing of materials and or parts and obviate the deficiencies of the prior art, it is an object of the present disclosure to present a novel method for non-destructively detecting defects in a manufactured item wherein the materials or parts that are subjected to cryogenic temperatures (cryogenic temperatures are typically considered temperatures approaching and below~-300° F., -184° C., 89° K, for the purposes of this disclosure, cryogenic temperatures may include temperatures lower than~-280° F.) or near-cryo temperatures (for purposes of this disclosure near-cryo temperatures may include temperatures approaching and below -70° F.). The method includes determining a first metric of the manufactured item at first temperature, where the first metric is a function of a measureable characteristic of the material; cooling the manufactured item to Cryogenic temperatures. Subsequent to the cryogenic cooling, a second metric representing based on the same characteristic of the manufacture item is determined at a second temperature. The method further includes comparing the first metric with the second metric; and, upon the comparison detecting the defect.

It is also an object of the disclosure to present a novel method for detecting unconverted austenite in steel. The method including determining a first metric representing at least one characteristics of a specimen at a first temperature; cooling the specimen to cryogenic temperature; and subsequent to the cryogenic cooling, determining a second metric representing the characteristic of the specimen at a second temperature. The method then compares the first metric with the second metric; and, detecting the unconverted austenite based upon the comparison.

It is still another object of the disclosure to present a novel method for correcting defects in a milled item. The method includes milling a part to predetermined specifications and then deforming the part by cooling the part to cryogenic temperatures. The method further includes heating the part to a first temperature; detecting the deformation; and, re-milling the milled item in response to the deformation to the predetermined specifications.

It is yet another object of the disclosure to present a novel method of detecting the transformation of retained austenite into martensite. The method includes applying ultrasonic waves to the manufactured product at a first temperature; and measuring the reflected wave and continuing the application of ultrasonic waves and measuring the reflected waves while incrementally reducing the temperature to cryogenic temperatures and heating above cryogenic temperatures, and comparing successive wave measurements to determine the transition based upon changes over successive increments of the measured waves.

An additional object of the disclosure, is to present a novel method for detecting a defect in a manufactured item. The novel method includes determining a characteristic of the manufactured item at first temperature; cooling the manufactured item to cryogenic temperatures according to an initial temperature time cycle and monitoring the manufactured item for acoustic emissions resultant from phase transition during the cooling. The method also includes recording the acoustic emissions and changing the temperature time cycle as a function of the emissions, then controlling the temperature of the manufactured item as a function of the new temperature time cycle. The method further determines a second metric representing the characteristic at a second temperature subsequent to the cooling; compares the first metric with the second metric; and, based on the comparison, any defects may be detected.

These and many other objects and advantages of the present subject matter will be readily apparent to one skilled in the art to which the invention pertains from a perusal of the claims, the appended drawings, and the following detailed description of preferred embodiments.

BRIEF DESCRIPTION OF THE DRAWINGS

FIG. 5 is an illustration of a temperature-time curve according to an embodiment of the disclosed subject matter.

DESCRIPTION

Figure 1:
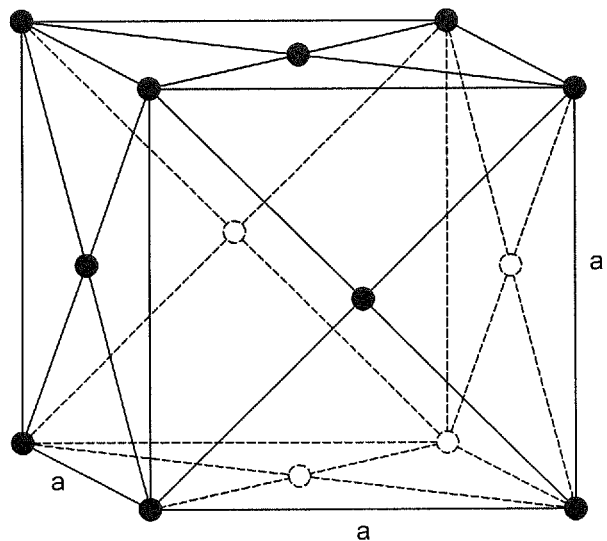
FIG. 1 is an illustration of the face centered cubic structure of Austenite.
Figure 2:
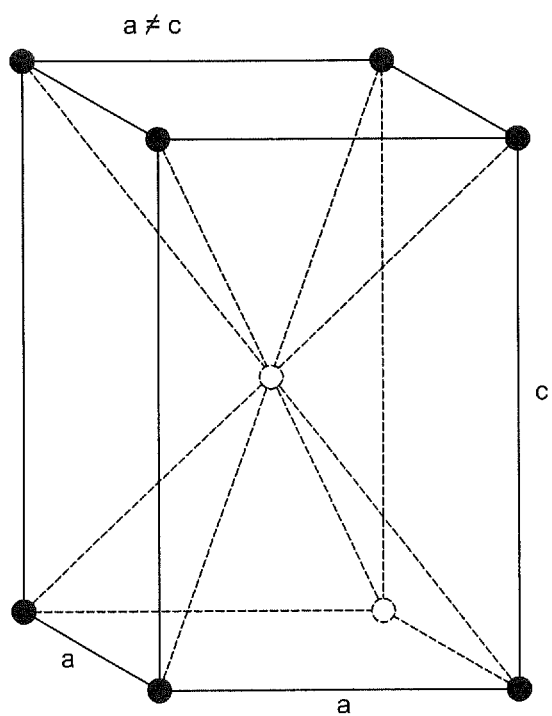
FIG. 2 is an illustration of the body centered cubic structure of Martensite.

The forgoing explanation of the system and method of cryogenic NDT testing, demonstrates a novel and effective means and methods for increased reliability of non destructive testing, both as a free-standing modality, and also as a synergistic element in company with other testing processes. The cryogenic NDT procedure may detect resonant frequency shifts resulting from changes in mass, stiffness or damping of a part. Defects such as cracks, voids, chips, modularity, porosity, variations in hardness, missed manufacturing processes, and de-lamination may be detected using the cryogenic NDT processed described herein.

The disclosed subject matter including a cryogenic NDT Process may be enabled with the use Liquid Nitrogen or Liquid Helium (or other mechanism to remove heat from the test material) to cool the test material to a cryogenic temperature and then heating to an elevated temperature. (exemplary ranges for cooling around minus −280 degrees Fahrenheit to minus −460 degrees Fahrenheit and exemplary ranges for heating around +280 degrees Fahrenheit to +465 degrees Fahrenheit)

Embodiments of the disclosed subject matter are applicable in evaluating and testing ferrous and non ferrous materials, including aluminum, plastics and composites and other materials. The testing process may include but not limited to testing for residual compressive and tensile stress, retained austenite and martensite and other discontinuities or anomalies.

During refrigeration to cryogenic temperatures, the free energy balance between retained austenite and martensite may be tipped in the favor of martensite and the diffusionless shear transformation (martensitic transformation) proceeds to near completion. Subsequent to the low temperature cycle of cryogenic processing the parts may be reheated to (+280 deg. F. to +465 deg. F.) and tempering changes the thus formed primary martensite into tougher tempered martensite.

Cryogenic processing may minimize the deleterious effects of both retained austenite and residual stress by accelerating the spontaneous changes that would occur in finished components that had not been treated and revealing material changes as a result thereof One method includes performing cryogenic processing on components that have been heat treated but not yet undergone a final machining Subsequently, any deformation, warping or distortion resulting from the acceleration of the spontaneous processes of the cryogenic processing may be removed in final machining. The application of the disclosed processed may reduce the bulk required of may pre-manufacturing blanks or slugs.

Following the disclosed testing process when applied to materials that contain residual stress with a resultant change in material density and volume, a visual distortion of geometry shape change may occur. This visual distortion is one of many property distortions that may occur as a result of such testing that reveal an anomaly, defect or property characteristic of the test material.

Figure 3:
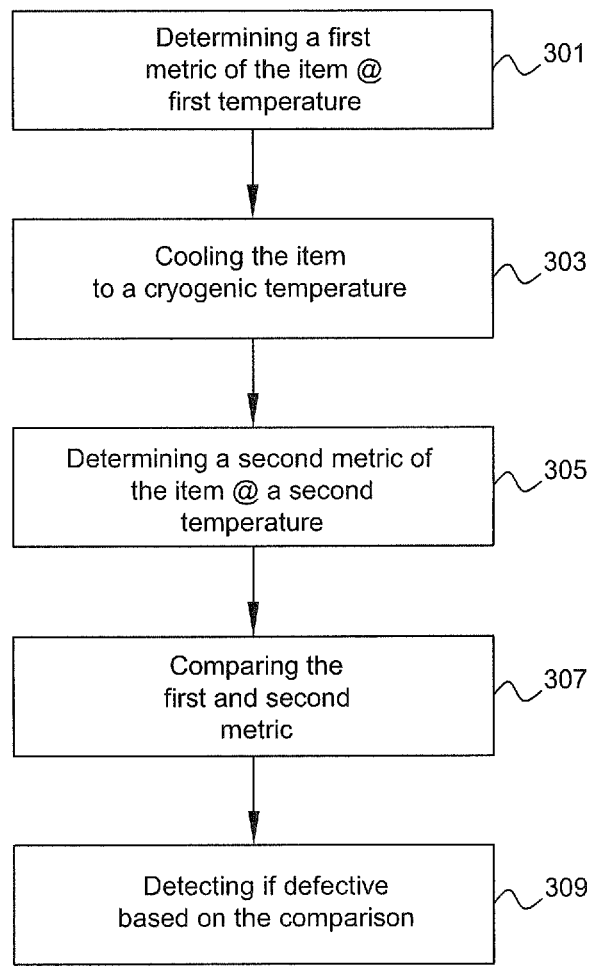
FIG. 3 is an flow chart for an embodiment of the disclosed subject matter for detecting defects in a manufactured article.

FIG. 3 is a generalized flow chart of a disclosed embodiment for detecting defects in a item. A reference metric of a characteristic of the item is determined at a reference temperature as shown in Block 301. The metric may be one derived from many measured characteristics or may be a series of metrics. The characteristic may be a characteristic of the manufactured item's dynamic response to an excitement or external force or an order of mechanical resonance. The characteristic may also be a static characteristics such a geometric dimension or density. In addition the characteristic may be one defined in the time domain. By way of example only, the characteristic may be obtained using Coordinate Measuring Machine (CMM), Optical Comparator, CAD System, Spring Tension and Compression Testers, Micrometers, Digital Indicators, Height & Depth Gauges, Surface & Contour Measuring Devices, Grade A Surface Plate/Plane Part Trueness, Run-Out Measurements, RA Surface Roughness and NDT Hardness Testers, and optical measuring devices.

After the metric or several metrics are determined the item is cooled to a cryogenic temperature as shown in block 303. The cryogenic temperature is preferably less than or equal to −280 Fahrenheit (~−174° C., 100° K or 179° R) and greater or equal to absolute zero (~460° F. For −273° C.). Cooling may be implemented with liquid nitrogen, helium or other known cooling source or method. The cooling may also be implemented according to a predetermined time-temperature curve which may include both cooling and heating cycles. Subsequent to the cooling the item may be heated to a second reference temperature, this heating may also be accomplished using a time-temperature curve. The heating may be advantageous to minimize the duration of the testing. Heating may also be used to heat the manufactured item to a predetermined high temperature above second temperature and allowing the manufacture item to cool to second temperature. Preferably the predetermined high temperature is greater or equal to 280 degrees Fahrenheit and less than or equal to 465 degrees Fahrenheit.

A second metric representing the same characteristic or characteristics or the reference metric may be determined at the second temperature as shown in Block 305. The second temperature may be at Cryogenic levels, may be at room temperature, or at the temperature at which the first metric was determined. The reference and second metrics may represent characteristics of cross section area, length, width, depth, height, tolerance, $N^{th}$ moment of area, and center of gravity. The reference and second metric may be determined using modal analysis, X-Ray diffraction, Magnetoelastic Barkhausen Noise measurement, Magnaflux Quasar process Compensated resonant Inspection, eddy currents, ultrasound, Digital Image Correlation, Laser Profilometer, Optical Profilomter, Moire Wave Light Synchotron Xray, Xray Diffraction, Barkhausen Noise, Metrotomography, 3 Dimension Strain Gauge, Neutron Diffraction, Holographic HNDT, Infrared Thermography, Martensite Examination using a Ferrometer (Ferrite Scope), Quartz Dilaometer, Michelson Laser Interferometer and Scanning Electron Microscope however such a list is not exhaustive and is not intended to be limiting.

The reference (first) and second metric may then be compared as shown in Block 307 and as a result of the comparison a defect or defects may be detected as shown in Block 309. The comparison may result in a gross difference, a percentage difference or other relevant statistic may be used with a threshold to determine the presence of a defect and the extent of the defect. For example a deviation of more than 1% may indicate a serious defect, where as a deviation of less than 0.01% may be considered a minor inconsequential defect. These percentages are only for illustrative purposes and are not necessarily indicative of actual thresholds. Deviations in the metrics may be a function of the transformation of retained austenite to martensite or as a function of the relative reaction of non homogenous material such as an item with a non-uniform distribution of austenite and martensite, or a function of discontinues within the item.

Figure 4A:
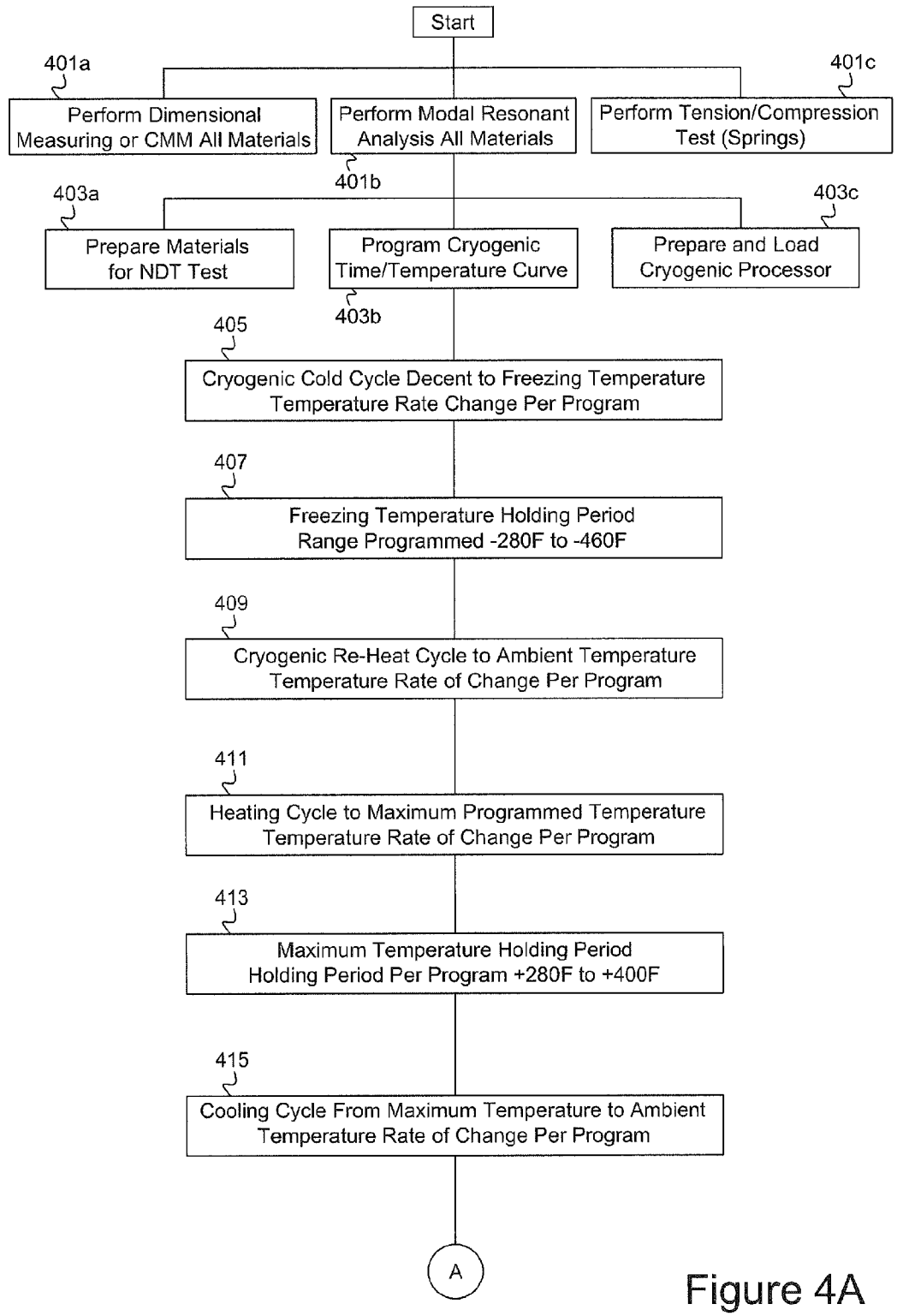
FIGS. 4a and 4b are an illustration of the apparatus for cryogenic testing according to an embodiment of the disclosed subject matter.
Figure 4B:
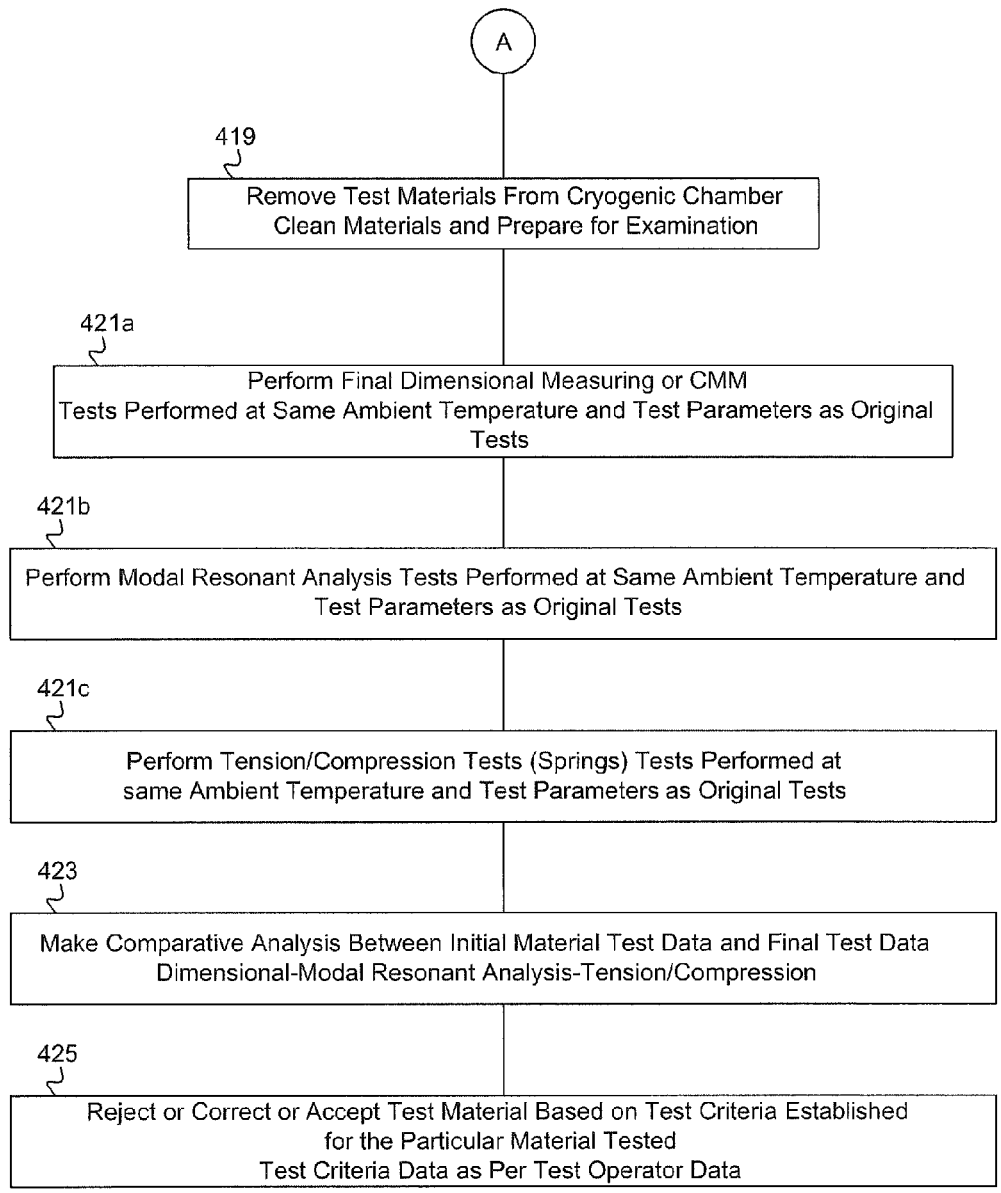

FIGS. 4a and 4b provide another illustrative flow chart of a process for non destructive testing NDT according to an embodiment of the disclosed subject matter.

The test material may be evaluated and documented with dimensional measurement, modal resonant analysis, or tension/compression tests as shown in Blocks 401a, 401b and 401c or other process to determine the existing structural dynamic or static characteristic of the mechanical structure of the material being tested. (i.e. Young's modulus and cross sectional geometry). The mechanical resonances may be documented and the pattern of summed sinusoidal deformations may be recorded using a spectrum analyzer following an excitation force imparted to the test material. Alternative methods for documenting structural dynamic characteristics may include Magnetoelastic Barkhausen Noise (BN) or Magnaflux Quasar Process Compensated Resonant Inspection (PCRI) or X-Ray Diffraction (XRD) or others.

The test material may be excited with a known and repeatable input. This input is typically generated by a controlled impact or actuator providing broadband or sinusoidal energy over the appropriate frequency range of analysis. The input may also be in the form of a field such as electric or magnetic fields, or light or thermal excitement.

The structural or field response of the test material to the applied input force may be captured using a dynamic sensor such as a microphone or accelerometer (vibration pickup) and a high speed analog to digital converter (ADC) with appropriate anti-aliasing filters. The acquired data may be used with a Fast Fourier Transform (FFT) for analysis in the frequency domain.

The frequency spectrum of the test material is analyzed and logged as a spectral template. Mechanical resonances may be indicated as peaks in the frequency spectrum of the response. This information may also be used as a comparative test or reference baseline to be performed following cryogenic cooling freezing cycle.

Dimensional and or physical shape mapping documentation of the test material may be performed using a Coordinate Measuring Machine (CMM), Optical Comparator, CAD System or other appropriate dimensional and hardness testing devices including but not limited to: Spring Tension and Compression Testers, Micrometers, Digital Indicators, Height & Depth Gauges, Surface & Contour Measuring Devices, light measuring devices, Grade A Surface Plate/ Plane Part Trueness, Run-Out Measurements, RA Surface Roughness, NDT Hardness Testers and other dimensional and surface testing devices. This information shall be logged as a template and used as a comparative test to be performed following the Cryogenic freezing and reheating cycle.

Materials to be tested may also go through a process whereby the materials are "Vibratory Stress Relieved" by applying Mechanical Cyclic Vibration energy to the test material with an exciter (force transducer) over a test frequency range while monitoring the damping effects of energy flowing into the material as a function of frequency using a spectrum analyzer. A plurality of orders of harmonic vibration absorption peaks are identified, each consisting of a plurality of vibration absorption resonant peaks, employing a vibration transducer having a response that is dampened to distinguish the harmonic peaks from the residual peaks. A sub-harmonic stress relief frequency is identified as a function of such frequency response and the composition of the part in question, and mechanical cyclic vibration energy is applied to the material for an extended time period at the sub-harmonic frequency identified. The frequency may vary in response to the frequency response of the material based on material specifications. This vibratory stress relief may be performed before or after Cryogenic processing.

The test material is then prepared for cryogenic cooling by thoroughly cleaning the test material with a suitable cleaner and application of a vapor inhibitor to prevent surface rusting or other chemical reaction and may be wrapped in metal foil as generally shown in Block 403a.

The cryogenic chamber/processor computer may be programmed with a "time temperature curve" to set the rate of temperature change of the test material, duration of the test material hold time at pre-set temperatures and temperature ranges as shown in Block 403b. The "time temperature curve" may vary based on the properties and type of test material being tested, the total mass, cross sectional properties and other data.

The test material is then loaded inside a cryogenic chamber/processor with spacing from other test materials to provide for ample air flow surrounding the test part as shown in Block 403c. Spacing of approximately 1 inch in small test specimens has been shown to be sufficient, in large test specimens larger spacing may be required.

The cryogenic chamber/processor computer is activated and the "time temperature curve" directs the discharge of the respective gaseous form of Liquid Nitrogen or Helium from the supply source(s) into the cryogenic chamber.

During the cryogenic cycle the "time temperature curve" may descend the temperature (cold cycle) of the test material from ambient room temperature to a temperature range varying between minus −280 degrees Fahrenheit to minus −460 degrees Fahrenheit using liquid Nitrogen or Helium as shown in Block 405. Certain temperature hold times may be pre-programmed in the "time temperature curve" to maintain the test material temperature at various temperatures as shown in Block 407.

Following the (cold cycle) of the cryogenic cycle the "time temperature curve" may direct the (re-heating cycle) of the test material back to either ambient room temperature as shown in Block 409 or to an elevated maximum temperature range varying between +280 degrees Fahrenheit to +465 degrees Fahrenheit as shown in Block 411.

Based on the pre-determined or pre-programmed "time and temperature curve" the chamber may hold the test parts at pre-determined temperature ranges as shown in Block 413 and cycle back to ambient room temperature as shown in Block 415.

Cryogenic cold, hold and re-heat cycles may be repeated with varying "time and temperature" curves based on the parameters of the specific materials test. The time and temperature curves are selectable/modifiable by the user.

Tests materials are removed from the chamber when the test materials have returned to ambient temperature and the cycle has been completed as shown in Block 419. The Metal foil may then be removed and parts may be thoroughly cleaned with a suitable cleaning material and dried.

Materials to be tested may also go through a process whereby the materials are "Vibratory Stress Relieved" by applying Mechanical Cyclic Vibration energy to the test material with an exciter (force transducer) over a test frequency range while monitoring the damping effects of energy flowing into the material as a function of frequency using a spectrum analyzer. A plurality of orders of harmonic vibration absorption peaks are identified, each consisting of a plurality of vibration absorption resonant peaks, employing a vibration transducer having a response that is dampened to distinguish the harmonic peaks from the residual peaks. A sub-harmonic stress relief frequency is identified as a function of such frequency response and the composition of the part in question, and mechanical cyclic vibration energy is applied to the material for an extended time period at the sub-harmonic frequency identified. The frequency may vary in response to the frequency response of the material based on material specifications.

The previous tests as described above may be repeated at the same room temperature and document results. Thus the test material may be evaluated and documented with dimensional measurement, modal resonant analysis, or tension/compression tests as shown in Blocks 421a, 421b and 421c or other process to determine the present structural dynamic or static characteristic of the mechanical structure of the material being tested. The second set of measurements while preferably done at room temperature, may be beneficially conducted at other temperatures including cryogenic temperatures. These measurements however may need to be adjusted for the temporary effects that result predominantly from cooling, rather than from phase transitions or imperfections.

Test data templates and final post testing results may be compared to determine and document any changes in test data as well as any changes in pre and post test data to the specification test limits on file for the respective test material as shown in Block 423.

Based on the comparison the test material may be rejected, corrected or accepted based on the criteria for acceptance, correction or rejection designed and approved for the respective test material as shown in Block 425.

Temperature Cycling

FIG. 5 is a graphical illustration of an exemplary time-temperature curve for use by some embodiments of the disclosed subject matter. The figure shows the temperature fluctuations from ambient temperature (room temperature) in degrees Fahrenheit over the course of 48 hours.

The test material undergoes a cryogenic cold cycle decent to −300° F. over an eight hour period as shown by 501. The test sample undergoes a freezing temperature holding period as represented by 503. A cryogenic re-heat cycle takes the temperature from −300° F. to ambient as shown by 505. From ambient temperature the sample under goes a heating cycle from ambient to a maximum programmed temperature in 507, which as shown in the figure is +300° F. The sample is held at the maximum programmed temperature at 509, is cooled back to ambient temperature at 511 and undergoes a 2nd heating cycle from ambient to the maximum programmed temperature as shown by 513 The sample is held at the maximum programmed temperature and cooled to ambient as represented by 515 and 517 respectively. As noted previously, this graphical representation is not exclusive and served only as an example, as to the order and sequence of cryogenic cooling and heat cycles and the times and temperatures illustrated.

Re Machining

Figure 6:
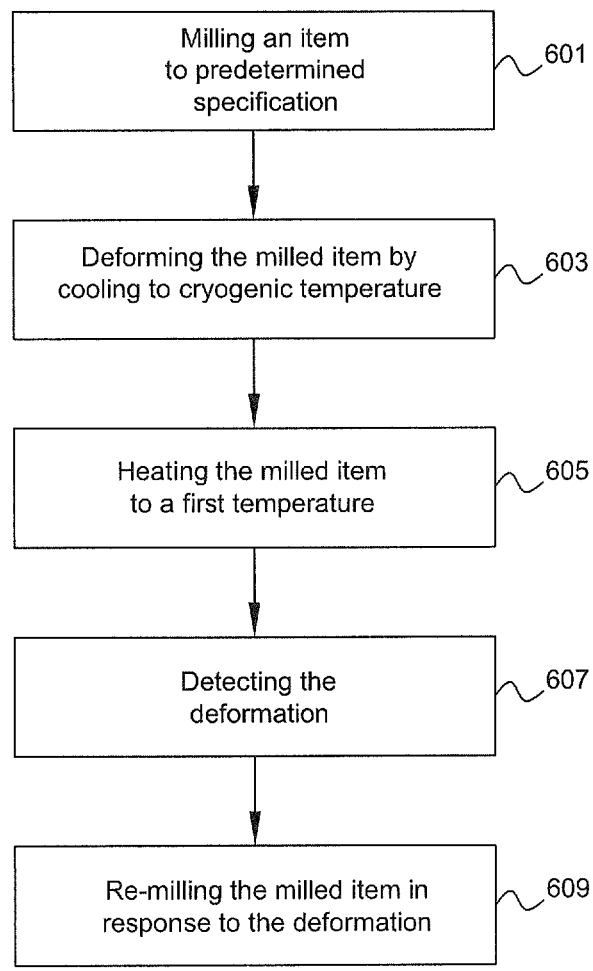
FIG. 6 is a flow chart for milling a manufactured item after a cryogenic induced deformation according to an embodiment of the disclosed subject matter.

FIG. 6 illustrates an embodiment in which the cryogenic NDT is used as part of the machining process, where the parts to be processed tested will first go through a complete NDT test procedure to ensure the quality. The parts are milled or machined to a predetermined specification as shown in Block 601. The geometry of the parts are then measured and a baseline will be established for the parts to be cryogenic NDT tested. As mentioned previously this not only provides a base line, but also ensures that the part was machined to the proper specifications.

The part is deformed by cooling in the cryogenic chamber to cryogenic temperatures as shown in Block 603. The part is then heated in the cryogenic chamber to a first temperature, typically ambient temperature as shown in Block 605. Once the cryogenic chamber has returned to room temperature following for example a −300 F cold cycle, a heat cycle of up to +300 F may also be executed on some parts applications and finally returned to ambient room temperature all under the control of computer programming.

The tested parts are then removed from the cryogenic chamber and the initial measurements that were performed on the parts are all performed for the second time in order to detect the deformation as shown in Block 607. The part's geometry, as measured the second time and any previous the test data will be compared to the initial data that was recorded prior to NDT cryogenic process testing.

The testing process may take place over a period of several days and is controlled by a computer that is programmed for a very slow rate of temperature change, and establishes the duration of temperature event cycles.

Should any part dimension change following the cryogenic NDT test process and are found out of dimension specifications, they will either be re-machined to proper specifications or replaced with another NDT stress relieved part meeting correct dimensional specifications as shown in Block 609.

While only one cooling cycle is described with respect to FIG. 6, multiple heating and cooling cycles may be applied. In addition the temperature cycles involve in the re-machining process as well as the other method described herein may be driven by the detection of phase transitions as described hereafter.

Phase Transition Detection

Figure 7:
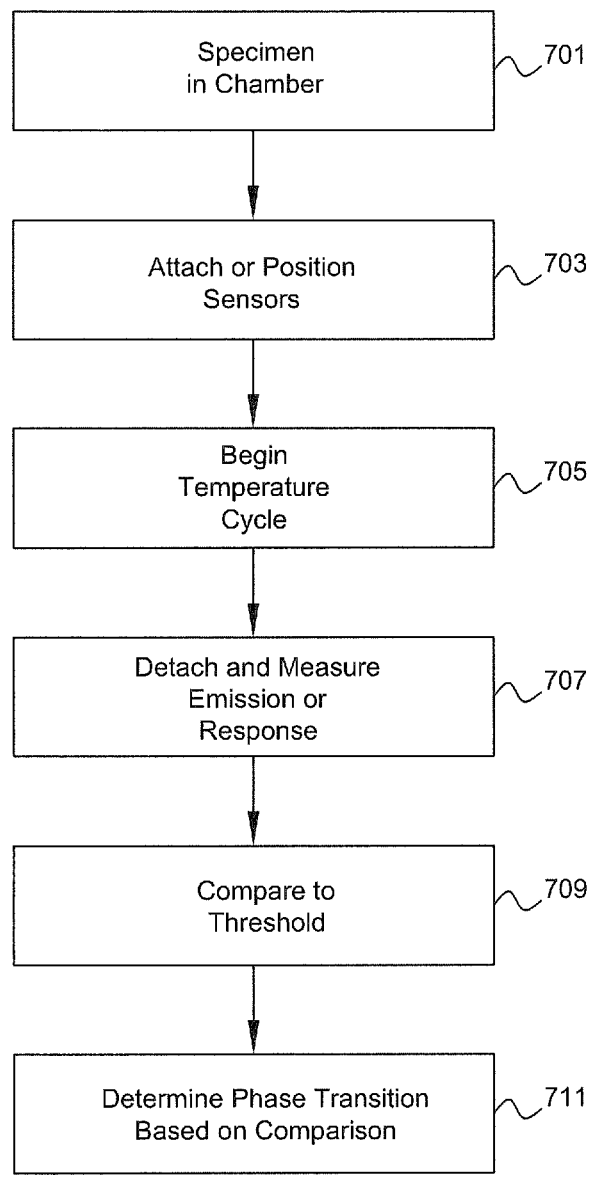
FIG. 7 is a flowchart for determining a phase change in a material according to an embodiment of the disclosed subject matter.

Additional information regarding determining the suitability of parts with respect to defects may also be determined as a function of the time and temperature at which phase transformation occurs. In an embodiment of the disclosed subject matter, the phase transformation process is monitored as to identify the time and temperature range where phase transformation or transition occur. FIG. 7 illustrates an exemplary method for determining the time and temperature (and duration at temperature) associated with the transition.

The test specimen or part is placed in the cryogenic chamber as shown in Block 701, and sensors are attached as shown in Block 703. As noted below because of the significant range of temperature change, the use of contactless sensors, such as EMATs is preferable. A cryogenic and/or heat cycle through a temperature range is undertaken as shown in Block 705. The temperature may also be held at a temperature for a given period of time at the phase transformation temperature zone identified, or cycle the parts back and forth below and above the phase transformation temperature zone. The phase transitions may occur beging lower than −70° F. and greater than 200° F. Upon detecting an acoustic emission, or change in response to the ultrasonic wave, the emission or response or delta from a prior emission or response a measurement of such is recorded as shown in Block 707 and compared to a threshold as shown in Block 709. As a result of this comparison the phase transition can be detected along with the corresponding time and temperature of its occurrence as shown in 711. It is also envisioned that the measurements may be filtered to remove noise and other spurious signals not associated with the phase transformation. Many types of filters may be employed in the measurement and comparison steps described with respect to the disclosed subject matter.

In a non-limiting example, a part is tested beginning at ambient temperature at 59 degrees F. and descending to −450 F over a 12 hour decent period, then held at −450 F for 12 hours, the part is then re-heat to ambient over a 8 hr period, then heated from ambient to +300° F. for 2 hours then descend back to ambient when done.

While performing the test procedure phase transformation may be detected using ultrasound or EMAT at (−150° F. to −170° F. degrees range). Thus the part may be held at −160° F. for 3 hrs as an example, and may cycle back and forth between −140° F. to −180° F. several times, and then continue to complete the test process. This process may be performed again on the re-heat cycle as the temperature climbs back up and goes through a phase transition temperature zone again between −150 F to −170 F as an example and hold the part temperature again for 3 hrs at −160 F as an example and then continue the test process as planned.

This same process may also be applied when we are on the ambient to +300 F heat cycle. If the phase transformation is detected in the +230° F. to +250° F. temperature range. The temperature may be held at +240° F. for a period of time and cycle back and forth between +220° F. and +260° F. and then continue as planned, and the time, degree and temperature of the phase transition begins, continues and is completed is recorded.

Exemplary Characteristics

As noted above the metric may be one derived from many measured characteristics or may be a series of metrics, or an array representing a field or measurement. The characteristic may be a characteristic of the manufactured item's dynamic response to an excitement or external force or an order of mechanical resonance. Characteristics envisioned in the current subject matter, include geometry, density, conductance, resistance, capacitance, inductance, magnetic flux density, magnetic resonance, electrical resonance, mechanical resonance, frequency response, stress, strain, reflection, refraction, absorption, modulus of elasticity, hardness, radiation, electric field, magnetic field, deformation, eddy currents, thermal coefficients of expansion. This list is not exclusive nor is it intended to be exhaustive.

Using finite element analysis to determine the residual stress as a result of the changed dimensions and determining reliability, the lifetime of part based on the comparison. The test method is also useful for quantifying the distribution bulk residual stress in three dimensional materials. As a material deforms during the cryogenic test process the surface contour deforms and may be plotted and analyzed using Finite Element Analysis similarly to how Prime utilizes contour testing to determine stress, however recognizing the present process is non-destructive. With this information the measure of residual stress may be calculated and fatigue life determinations may be made. After a material is cryogenic tested the process may be re-applied a second time to the material following a re-machining corrective procedure and comparative analysis may be applied again to determine residual stress changes.

Acoustic emissions, refers to the generation of transient elastic waves during the rapid release of energy from localized sources within a material. The source of these emissions in metals is closely associated with the dislocation movement accompanying plastic deformation and the initiation and extension of cracks in a structure under stress. However other sources of acoustic emissions is the phase transformation of the material, it is this source of emissions that may be used in the cryogenic NDT processes as described above. These acoustic emission may be captured using Electromagnetic Acoustic Transducer (EMAT) or a piezoelectric transducer.

The elastic constants and corresponding velocities of sound in a material are described in terms of Hooke's law wherein an elastic constant relates a linear stress to a linear strain. The elastic constants are functions of the thermodynamic state of the material and the interatomic binding forces in the crystal lattice. Transitions of the first and second order invariably produce measurable velocity changes that can be correlated to the specific mechanisms that cause the anomalies.

Ultrasonic Attenuation may also be use to indicate a material defect or retained austenite, The reaction of a crystalline solid to a stress wave does not obey fully the elastic stress-strain relationship of Hooke's law. Any solid medium possesses nonlinear or anharmonic features that give rise to higher order coefficients in the strain-energy function. The nonlinear effects in a crystal lattice are related to third-or higher-order terms in the strain-energy expression. These features also result in sound absorption or attenuation in a solid.

The term ultrasonic attenuation incorporates losses of sound energy due to scattering and absorption processes. Scattering is caused mainly by imperfections and anisotropy of elastic constants.

EMAT is a transducer for non-contact sound generation and reception using electromagnetic mechanisms. EMAT is an ultrasonic nondestructive testing (NDT) method where couplant is not needed since the sound is directly generated in the material underneath the transducer. Due to this couplant free feature, EMAT is particularly useful for the NDT applications of automated inspection, hot and cold environments. The EMAT may also allow the use of conventional ultrasonic, Phase Array Ultrasonic, Immersion ultrasonic and Laser Ultrasonic.

A piezoelectric sensor may also be used to capture the Acoustic emission. A piezoelectric transducer is a device that uses the piezoelectric effect to measure pressure, acceleration, strain or force by converting them to an electrical signal.

Acoustic resonant inspection works on the principle that every part has a unique vibration signature (resonant frequencies). These resonant frequencies will have little change from good part to good part. However they will shift when there is an internal or external change in the part, such as a phase shift from austenite to martensite, or a change in geometric or retained stress characteristics, or discontinuity.

To determine a parts vibration signature, a striker will contact the part and a sensor (microphone) may record the resonant frequencies generated on a full domain spectrum analyzer. These frequencies of a vibration signature may form the basis of the first and second metrics.

Strain gauges may also be used to detect Acoustic emissions, ultra sonic response and vibration response, in addition to deformation as may lasers Linear and other electromagnetic sensors and/or transducers.

Apparatus and Set Up

Figure 8:
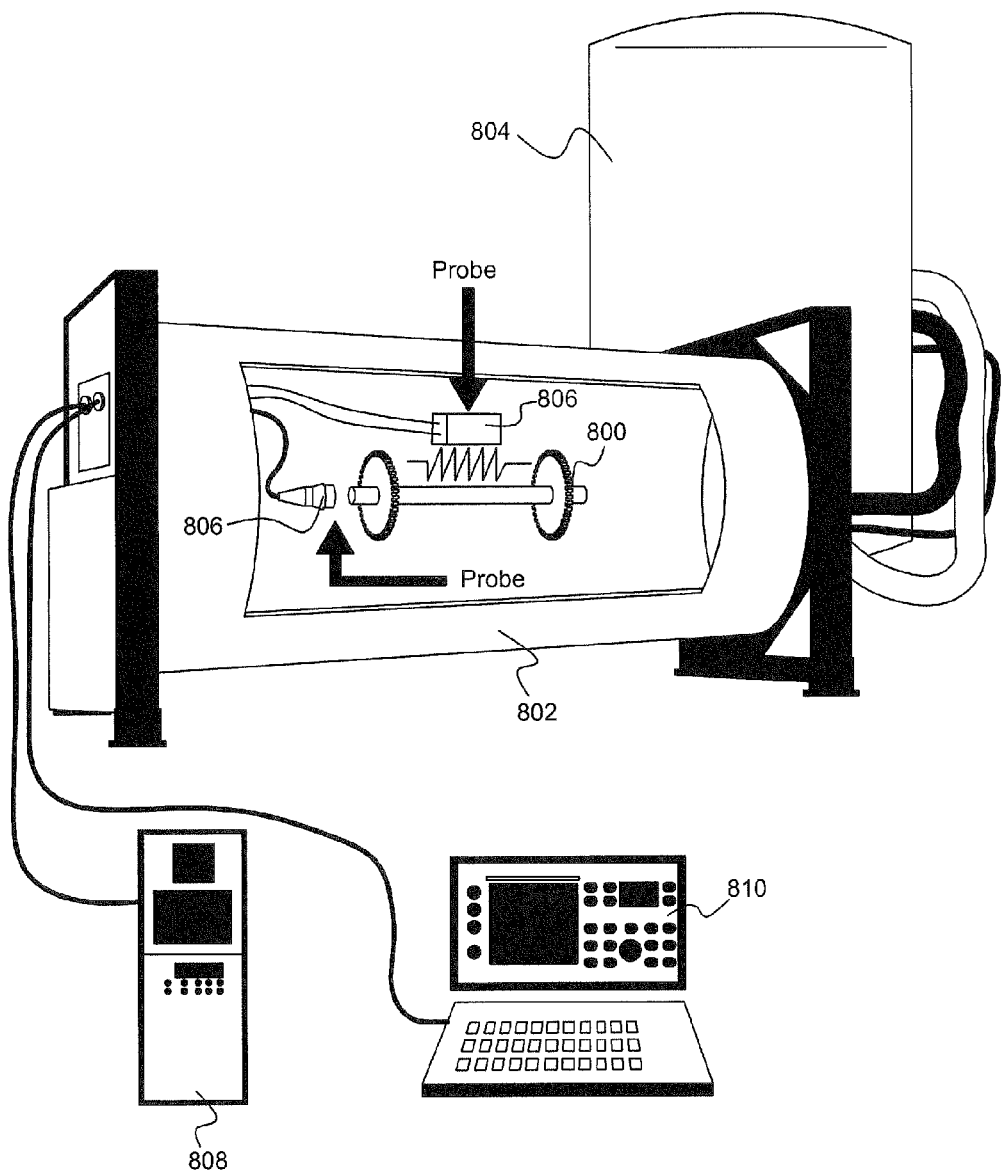
FIG. 8 is a schematic representation of a cryogenic processing system for cryogenic NDT according to an embodiment of the disclosed subject matter

Performing the Cryogenic NDT Process takes very specialized equipment with highly skilled technicians. FIG. 8 is an illustration of a exemplary equipment for use in performing cryogenic NDT according to some embodiments As shown in FIG. 8, the test material 800 is contained within a cryogenic processing chamber 802. A liquid Nitrogen, or liquid Helium tank 804 is connected to the chamber 802 for the cooling, and a heat source(not shown) is also operationally connected to the Chamber 802 for heating the test material. FIG. 8 also shows a plurality of probes 806 in the chamber 802. While determining the metrics at cryogenic temperatures in some embodiments is not necessary, in some embodiments of the disclosed subject matter determining the response or material characteristics during the cryogenic cooling is advantageous. While not shown, temperature, pressure and other characteristics within the chamber are advantageously sensed and used by the cryogenic chamber controller 808 to control the environment inside the chamber during testing. An analyzer 810 captures the sensed responses and characteristics of the test material 800 during the testing and also advantageously corresponds the response and characteristics of the test material 800 with the environment within the chamber. This correspondence may be effectuated with an operation connection between the analyzer and controller, or by the use of time stamps in the controller and the analyzer.

Peripherals

Figure 9:
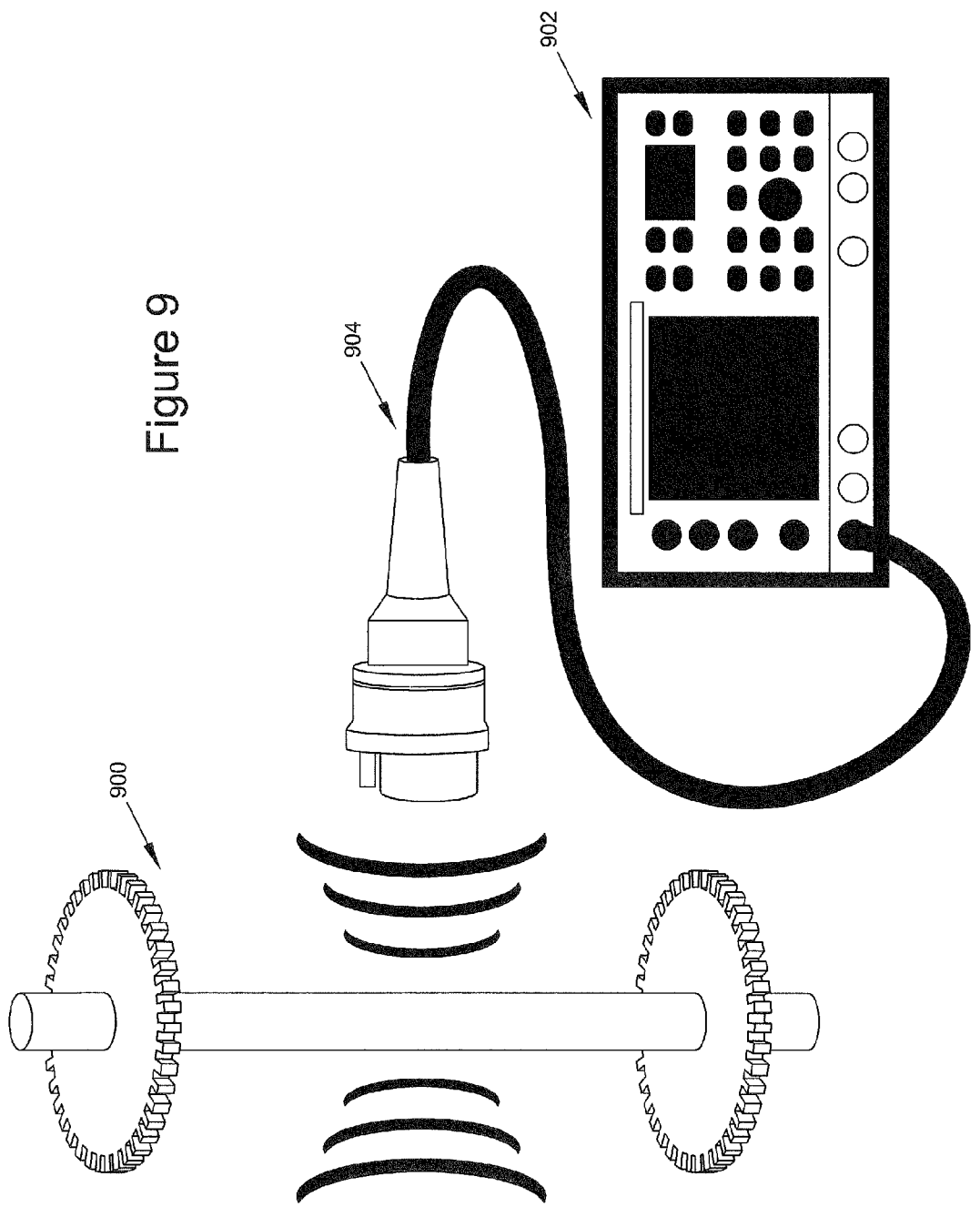
FIG. 9 is a schematic representation of a spectrum analyzer according to an embodiment of the disclosed subject matter.
Figure 10:
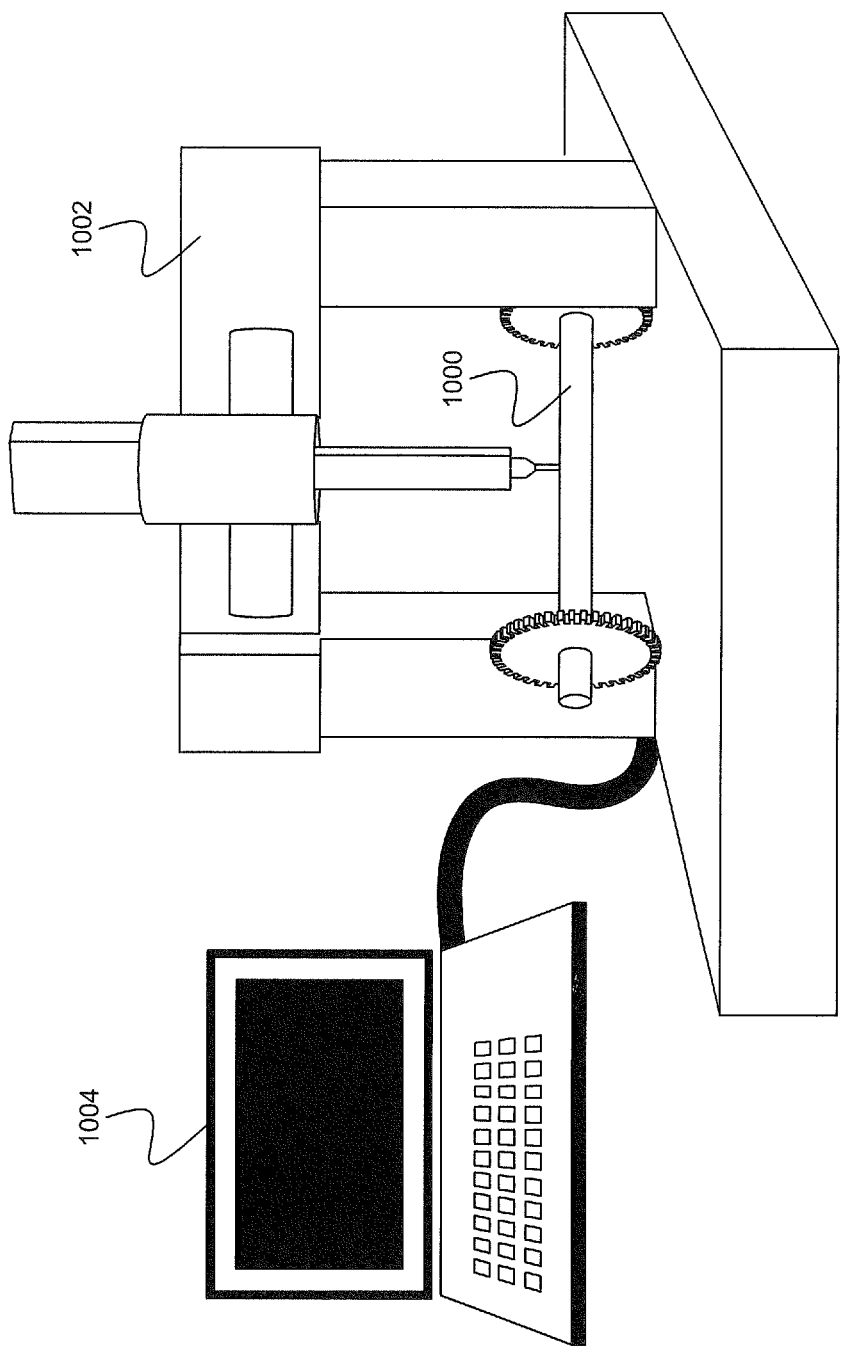
FIG. 10 is a schematic of a coordinate measuring machine used with an embodiment of the disclosed subject matter.
Figure 11:
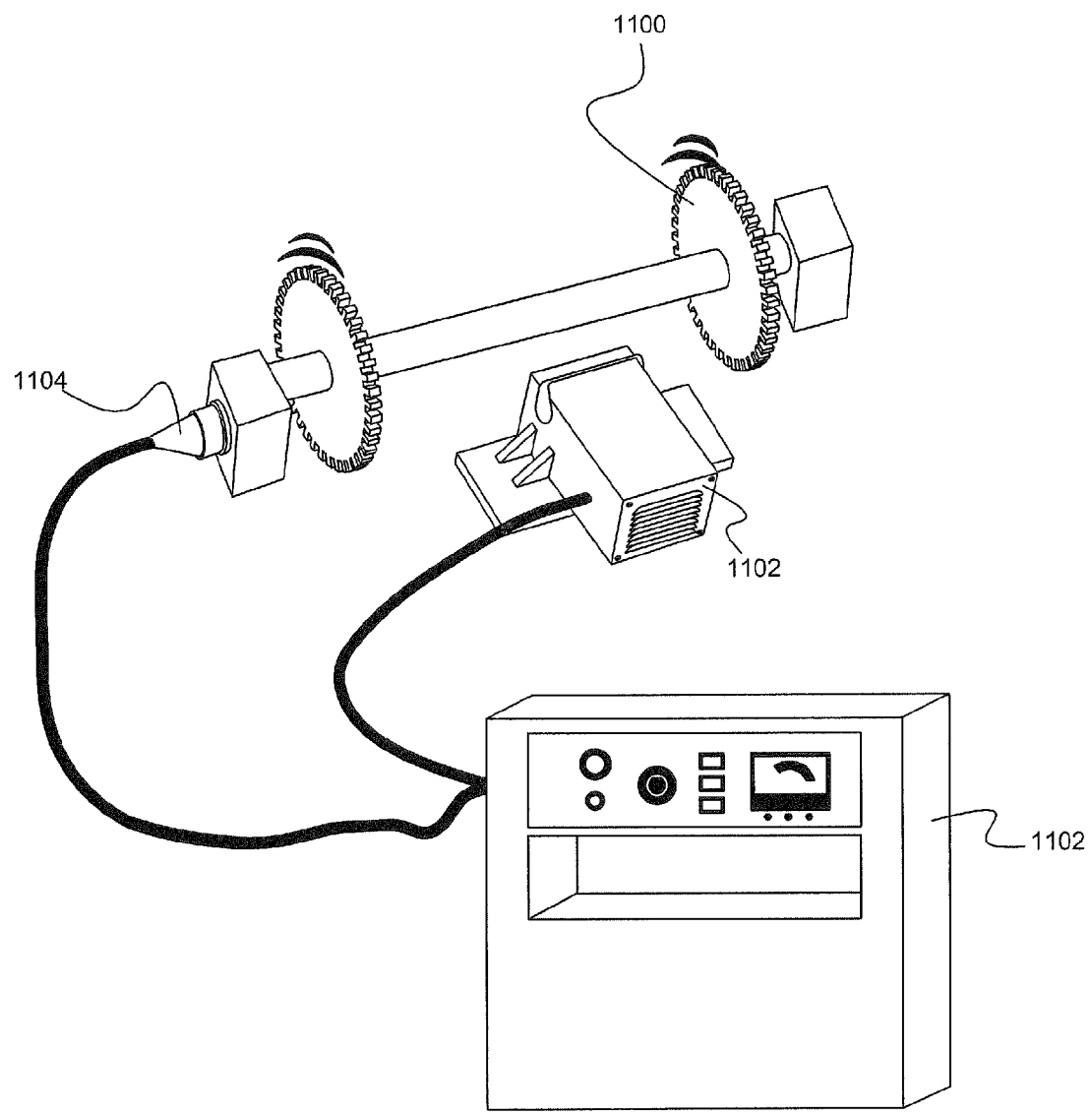
FIG. 11 is a schematic of an apparatus to induce vibrations in a test specimen according to an embodiment of the disclosed subject matter.

Various apparatus and systems may be used in conjunction with the cryogenic NDT process as disclosed. FIGS. 9, 10 and 11 show a spectrum analyzer, a coordinate measuring machine and vibration analyzer systems.

FIG. 9 is a generalized spectrum analyzer 902, with a dynamic Sensor 904 for measuring a dynamic response to a stimulus of the Test material 900. As noted previously, the response may be in the form of a frequency, magnetic field, electric field, reflection/refraction of a wavelength, attenuation, resistance and/or conductivity.

As shown in FIG. 10, a coordinate measuring machine 1002 may be advantageously used to determine the geometric properties of the test material 1000. A processor 1004 is typically used in conjunction with or as part of the coordinate measuring machine 1002. The geometric properties of the test material 1000 as discussed above may be used to determine first and second metrics of the test material 1000.

As shown in FIG. 11, the test material 1100 is excited by a vibration exciter 1102. The vibratory response is captured by a vibration transducer 1104. The response may be processed in the Vibration Spectrum analyzer 1106 to determine the first or base line metric, as well as the second metric. The Vibration Spectrum analyzer 1106 may, like many other analyzer/controller described herein, take the form of a generalized computer or processor running specialized software, or may be a dedicated piece of hardware such as an application specific integrated circuit. In addition the vibration exciter 1102 may be used as discussed elsewhere for vibratory stress relief in conjunction with the cryogenic NDT.

Aspects

The present subject matter provides a useful alternative method for non-destructive testing of such metallic and non metallic components, and also can serve as a supplement to other non destructive testing modalities, so that in such application, cryogenic testing can aid the manufacturer and/or assembler to reach a more reliable level of confidence in component reliability and strength. This can be obtained through the disclosed system and method through calibrated cryogenic immersion and subsequent examination by optically enhanced as well as human eye examination, in addition to synergy between such cryogenic analysis and other means of non destructive testing, even including x-ray. One value of cryogenic examination modalities is that appearance changes resultant from the cryogenic process as hereinafter described and thus provide the manufacturer with visible indicators or measurable statistics where differing levels of contaminant or other anomaly are present, this in addition to indicators which may be determined, such as resonance, conductance, hysteresis, attenuation, emissions, reflection, refraction and other non visible indicators.

Another aspect of the disclosed subject matter is temperature cycling associated with cryogenic processing may also be used to relieve residual stresses. During cooling, the crystal lattice contracts. Because heat transfer is from the surface of the treated component and because the temperature of the surface is changing with time a temperature gradient is established extending from the surface toward the core. This gradient causes a differential contraction between adjacent layers in the crystal, which, in turn sets up mild induced stresses. This stress causes dislocations to move through the crystal lattice. When moving dislocations of opposite sign collide they cancel out. Upon heating, the direction of the temperature gradient, the induced stresses, and the direction of dislocation movement are reversed and additional cancellation of dislocation occurs. This reduction in dislocation density may cause residual stress relief.

For example a new machined engine crankcase was placed on a grade A Granite Surface Plate and documented that the parting halves were perfectly flat. After the crankcase went through the −300 F Cryogenic NDT Process it was then again placed on the same surface plate and measured again. It was found that the crankcase geometry then shifted to its relaxed or stress relieved state and was found to have twelve thousandths of an inch deviation in surface flatness across the parting surface.

If this same crankcase were to have been installed in an engine without being stress relieved, over a period of time as the part was subjected to expansion and contraction in normal use, this residual metal stress could attempt to shift the part geometry to its relaxed metal state. This could cause crankcase cracking; uneven pressures on the engine bearings, increased engine friction, reduction of power and oil leaks to occur.

As a comparison, after the crankcase, a crankcase that showed signs of stress relieving by a change in geometry after undergoing the −300 F cryogenic NDT process was re-machined, and subsequently the part remained flat and did not distort during normal engine operation from residual stress. The result of the process is a reduction in case cracking susceptibility, even crankcase bearing pressures, decreased engine friction, improvement in power and improved fatigue life of parts.

Another aspect of the disclosed subject matter is the use of Finite element analysis to model the manufactured item and the quantized the deformation and residual stresses. The use of Final element analysis to categories the deformations enables not only reliability evaluation, but mode of failure analysis as well.

The mechanisms described above relative to stress relief by cryogenic process cycling apply to ferrous alloys, non ferrous alloys, and non metallic crystals and to even to some partially metallic crystals.

In addition to temperature and time curves discussed above, the variation of pressure independently or congruently may also be included in the cryogenic NDT process. Such low pressure or vacuum testing with respect to Space applications and high pressure testing with respect to hull inspections of deep sea exploration vehicles may be especially advantageous to the Cryogenic NDT process.

An aspect of the disclosed subject matter is the use of alternative cooling and heating methods. While the cooling discussed above examples utilized liquid Nitrogen and Liquid Helium a number of other cooling and heating techniques are envisioned to be compatible with the process. Such an example is the use of Adiabatic Demagnetization Refrigeration.

A different aspect of the disclosed subject matter includes the use of the Cryogenic NDT on plastics and composite materials. In composite structures the bond between the constituent parts when subjected to cryogenic temperatures may yield thus revealing a structural defect in the product. The yielding of the bond along with the constituent characteristics enable the determination of a defect.

A yet different aspect of the disclosed subject matter is the detection of precipitation hardening in the range of 220° F. to 465° F. in the heating cycle of the described NDT process. The detection of the precipitation hardening may influence the time temperature cycle or may be used as a characteristic.

A still different aspect of the disclosed subject matter may include the characteristic of mechanical shock susceptibility at cryogenic or other temperatures on the test material. The specimen may be shocked or excited by the use of light, sound, mechanical striker, heat, magnetism or vibration. During the excitement of the specimen the disclosed subject matter contemplates monitoring with real-time test apparatus such as acoustic ultrasonic or EMAT or LVDT quartz dilatometer or Michelson laser interferometer to determine the nature and degree of response.

Uses

The present subject matter relates to cryogenic NDT testing for metallic materials used on all ferrous and non ferrous alloys, springs and castings that respond to heat treatment, in addition to many other non-metallic materials and composite materials. Applications of the process include but are not limited to:

Piston, Diesel, Turbine, Jet, Turbojet, Turbofan, Turboprop, Aerospace, Satellite, Missile and Rocket Propelled Engines and Parts for Aircraft, Airline, Rocket, Rotor Wing Helicopter and Space Vehicles; Metallic materials used in the fabrication, construction, rebuilding/restoring of Piston, Diesel, Turbine, Jet, Turbojet, Turbofan, Turboprop, Aerospace, Satellite, Space Telescopes, Telescope Mirrors, Spacecraft, Astronomy, Missile and Rocket Propelled Engines, Airframes and Aircraft; National Aeronautics and Space Administration (NASA), Automotive, Truck, Bus, Firefighting, Agricultural, Forestry, Oil & Gas, Railway, Utility, Tractor, Trailer, Cranes, Motorcycle, Earth Moving Equipment, Tanks, Ships, Pumps, Boats, Submarine, Ocean Liner, Drilling Wells, Machinery, Electronic, Power Generators, Power Plants and Wind Turbine Generators/Transmissions/Propellers and parts used in the fabrication, deep sea exploration vehicles, oil and gas piping industry ,construction, rebuilding/restoration of those mentioned herein are envisioned to be advantageously tested using the cryogenic method described herein.

Computer, Telecommunications, Electrical, Pneumatic, Presses, Hydraulic, Mining, Construction Equipment, Undersea Exploration, Springs, Machine Industry, Metal Working Industry, Printing, Home Appliance, Golf Clubs, Musical Instruments, Acoustic, Bio Medical, Medical, Dental, Audio & Stereo, Artillery, Defense, Army, Navy, Air Force, Guns, Rifles, Shotguns, Canons, Weapons, Knives, Cutting Devices, Sporting Goods, Navigation Equipment, Testing Devices, Laboratory Equipment, Metal Housings, Metal Shafts, Bearings and all parts used in the fabrication, construction, rebuilding/restoration of those mentioned herein are envisioned to be advantageously tested using the cryogenic method described herein.

Solar Panel Systems, Lasers, Optical Systems, Orbital Optic Systems, Nano-Technology Applications, Filters, Elements, Alloys, Heat Treating, Ball Bearings, Pipes, Valves, Refrigeration, Cryogenic Applications, Metal Fabrication, Optoelectronics, Laser Tunnels, Welding, Ovens, Heating Systems, Air Conditioning Systems, Blowers, Fans and all parts used in the fabrication, construction, rebuilding/restoration of those mentioned herein, are envisioned to be advantageously tested using the cryogenic method described herein.

Crankshafts, Counterweights, Pins, Connecting Rods, Cylinders, Engine Blocks, Camshafts, Lifters, Pistons, Bearings, Valve Springs, Splines, Piston Rings, Crankcases, Housings, Attachments, Gears, Oil and Fuel Pumps, Air Compressors, Alternators, Generators, Bolts & Nuts, Hardware, Bearings, Turbine Blades, Spindles, Turbochargers, Engine Accessories, Blowers, Superchargers, Ignition Systems, Transmissions, Drive Shafts, Wheels, Brakes, Brake Rotors, Pinions, Steering Mechanisms, Propellers, Aircraft Turbine, Turbojet, Turboprop, Turbofan & Jet Engines, Aerospace Engines, Rocket and Missile Engines, Tank, Tractor Engines and Vehicle Transportation Equipment are envisioned to be advantageously tested using the cryogenic methods described herein.

In the competition racing industry, Engine, Transmission, Drive Trains, Suspension Springs, Frames, Brake Rotors and other parts utilized in building or overhaul/repair/restoration of but not limited to Quad Vehicles & Racing Engines, Motorcycles & Racing Engines, Indy Car Vehicle & Engines, NASCAR Vehicles & Engines, NI-IRA Dragsters Vehicles & Engines, AA Top Fuel Dragsters & Engines, Aircraft Airframe & Racing Engines for Vintage and Current Production General Aviation Certified, Sport and Experimental Category Aircraft, Vintage Auto Racing Vehicles & Engines, Can-Am Vehicles & Engines, Sports Prototype Vehicles & Engines, Formula One Racing Cars & Racing Engines, Offshore Boats & Racing Engines, Rocket Cars and Engines, Land Speed Vehicles & Engines, Vintage Automobiles & Engines would find benefit in the disclosed methods.

The tooling Industry, including Broaches, Reamers, Drills, Dies, End Mills, Saws, and Cutters are envisioned to be advantageously tested using the cryogenic method described herein.

Exemplary applications of the disclosed subject matter (not exhaustive list) include: Cryogenic NDT, Cryogenic parts testing, Cryogenic materials NDT testing, Cryogenic testing, Cryogenic NDT (non destructive testing) for residual stress, Cryogenic residual stress testing, Cryogenic compressive and tensile residual stress test, Cryogenic NDT compressive and tensile residual stress test, Cryogenic test for retained austenite, Cryogenic NDT test for retained austenite, Cryogenic test for retained martensite, Cryogenic NDT test for retained martensite, Cryogenic acoustic resonance test, Cryogenic NDT acoustic resonance test, −300° F. cryogenic non destructive testing, −450° F. cryogenic non destructive testing, −300° F. cryogenic NDT process, −450° F. cryogenic NDT process, Liquid helium cryogenic testing, Liquid helium cryogenic NDT testing, Liquid nitrogen cryogenic testing, Liquid nitrogen cryogenic NDT testing, Cryogenic nitrogen testing, Cryogenic nitrogen NDT testing, Cryogenic helium testing, Cryogenic helium NDT testing, Cryogenic test for heat treated materials, Cryogenic NDT test for heat treated materials, Cryogenic testing for residual stress, Cryogenic NDT for residual stress, Cryogenic acoustic NDT testing, Cryogenic vibratory NDT, Cryogenic vibratory non destructive testing, Cryogenic vibratory residual stress NDT, Cryogenic vibratory stress relief testing, Cryogenic vibratory stress NDT testing, Cryogenic vibratory stress relief NDT, Cryogenic vibratory acoustic resonance testing, Cryogenic vibratory resonance testing and Cryogenic vibratory resonance NDT.

It is noted that item(s), part(s), specimen(s), component(s), piece(s), sample(s), product(s) and material(s) have been used interchangeable throughout the specification. A distinction between terms above absent regard to the context of such use should not be implied, as these terms are directed to the object which is the subject of the testing described herein.

While preferred embodiments of the present invention have been described, it is to be understood that the embodiments described are illustrative only and that the scope of the invention is to be defined solely by the appended claims when accorded a full range of equivalence, many variations and modifications naturally occurring to those of skill in the art from a perusal hereof.

What I claim:

1. A method for detecting a defect in a manufactured item, comprising:
    determining a first metric representing at least one characteristic of the manufactured item at first temperature;
    cooling the manufactured item to a cryogenic temperature;
    heating the manufactured item to a second temperature subsequent to the cryogenic cooling;
    determining a second metric representing the at least one characteristic of the manufacture item at a second temperature subsequent to the cryogenic cooling;
    comparing the first metric with the second metric; and,
    detecting the defect based upon the comparison;
    wherein the first temperature is greater or equal to 32 degrees F.;
    wherein the step of heating the manufactured item to the second temperature includes heating the manufactured item to a predetermined high temperature above second temperature and allowing the manufacture item to cool to second temperature;
    wherein the predetermined high temperature is greater or equal to 150 degrees Fahrenheit and the cryogenic temperature is −70 F or colder.

2. The method of claim 1, wherein the at least one characteristic is a characteristic of the manufactured item's dynamic response to an excitement.

3. The method of claim 2, wherein the at least one characteristic is mechanical resonances.

4. The method of claim 1, wherein the at least one characteristic is a static characteristic of the manufactured item.

5. The method of claim 4, wherein the at least one characteristic is obtained via one of the group consisting of Coordinate Measuring Machine (CMM), Optical Comparator, CAD System, Spring Tension and Compression Testers, Micrometers, Height & Depth Gauges, Surface & Contour Measuring Devices, Grade A Surface Plate/Plane Part Trueness, Run-Out Measurements, RA Surface Roughness and NDT Hardness Testers.

6. The method of claim 1, wherein the characteristic is an electromagnetic field pattern.

7. The method of claim 1, wherein determining the first and second metrics comprises modal analysis, X-Ray diffraction, Magnetoelastic Barkhausen Noise measurement, Magnaflux Quasar process Compensated resonant Inspection.

8. The method of claim 1, wherein the cryogenic temperature is less than or equal to −70 Fahrenheit.

9. The method of claim 8, wherein the cryogenic temperature is less than or equal −280 degrees Fahrenheit.

10. The method of claim 1, wherein the cooling is according to a predetermined time-temperature curve.

11. The method of claim 10, wherein the predetermined time-temperature curve comprises a plurality of cooling and heating cycles.

12. The method of claim 1, wherein the heating is according to a predetermined time-temperature curve.

13. The method of claim 1, wherein the predetermined high temperature is greater or equal to 280 degrees Fahrenheit.

14. The method of claim 1, wherein the steps of determining a first metric and second metric each comprise:
    exciting the manufactured item, and measuring the resonance response.

15. The method of claim 14, wherein the measuring the resonance response comprises summing sinusoidal deformations.

16. The method of claim 1, wherein the first and second temperatures are room temperature.

17. The method of claim 1, wherein the first and second temperatures are approximately equal.

18. The method of claim 1, wherein the second temperature is greater than 32 degrees Fahrenheit.

19. The method of claim 1, wherein the second temperature is a cryogenic temperature.

20. The method of claim 1, wherein the cryogenic temperature is determined as a function of detected acoustic emission.

21. The method of claim 20, further comprising fluctuating the temperature above and below the cryogenic temperature until the acoustic emissions are reduced.

22. The method of claim 1, wherein the determining the reliability of the item is based on the comparison.

23. A non-destructive method for detecting a defect in a manufactured item comprising:
    determining a first metric representing at least one characteristic of the manufactured item at first temperature;
    cooling the manufactured item to a cryogenic temperature;
    heating the manufactured item to a second temperature subsequent to the cryogenic cooling;
    determining a second metric representing the at least one characteristic of the manufacture item at a second temperature subsequent to the cryogenic cooling the at least one characteristic;
    comparing the first metric with the second metric; and,
    detecting non-destructively the defect based upon the comparison;, wherein the first and second metrics represent characteristics selected from the group consisting of cross section area, length, width, depth, height, tolerance, nth moment of area, and center of gravity;
    wherein the step of heating the manufactured item to the second temperature includes heating the manufactured item to a predetermined high temperature above second temperature and allowing the manufacture item to cool to second temperature;
    wherein the predetermined high temperature is greater or equal to 150 degrees Fahrenheit and the cryogenic temperature is −70 F or colder.

24. A method for detecting unconverted austenite in steel:
    obtaining a specimen of heat treated steel;
    determining a first metric representing at least one characteristics of the specimen at a first temperature;
    cooling the specimen to a cryogenic temperature;
    heating the specimen to a second temperature subsequent to the cryogenic cooling;

determining a second metric representing the at least one characteristic of the specimen at a second temperature subsequent to the cryogenic cooling;

comparing the first metric with the second metric; and, detecting the unconverted austenite based upon the comparison;

wherein the step of heating the specimen to the second temperature includes heating the specimen to a predetermined high temperature above second temperature and allowing the manufacture item to cool to second temperature;

wherein the predetermined high temperature is greater or equal to 150 degrees Fahrenheit and the cryogenic temperature is −70 F or colder.

25. The method of claim 24, wherein the first and second metrics represent characteristics selected from the group consisting of cross section area, length, width, depth, height, tolerance, nth moment of area, resonance, nth moment of inertia, center of gravity.

26. The method of claim 24, wherein the cryogenic temperature is less than or equal to −280 Fahrenheit.

27. The method of claim 24, wherein the heating is according to a predetermined time-temperature curve.

28. The method of claim 24, wherein the predetermined high temperature is greater or equal to 280 degrees Fahrenheit.

29. The method of claim 24, wherein the first and second temperatures are room temperature.

30. The method of claim 24, wherein the first and second temperatures are approximately equal.

31. The method of claim 24, wherein the first and second temperatures are greater than 32 degrees Fahrenheit.

32. The method of claim 24, wherein the cryogenic temperature is a function of acoustic emissions from the specimen.

33. The method of claim 32, wherein the first and second temperatures are greater than 32 degrees Fahrenheit.

34. The method of claim 24, wherein the second temperature is a cryogenic temperature.

35. A method for correcting defects in a milled item;

milling an item to predetermined specifications;

deforming the milled item by cooling the milled item to a predetermined cryogenic temperature and heating the milled item to a first temperature;

detecting the deformation; and, re-milling the milled item in response to the deformation;

wherein the step of heating the milled item to a first temperature includes heating the milled item to a predetermined high temperature above the first temperature and allowing the manufacture item to cool to second temperature;

wherein the predetermined high temperature is greater or equal to 150 degrees Fahrenheit and the cryogenic temperature is −70 F or colder.

36. The method of claim 35, wherein the first temperature is room temperature.

37. The method of claim 35, wherein the deformation is a geometric change in dimension of the milled item.

38. The method of claim 35, wherein the cryogenic temperature is less than or equal to −280 degrees Fahrenheit.

39. The method of claim 35, wherein the heating is according to a predetermined time-temperature curve.

40. The method of claim 35, wherein the predetermined high temperature is greater or equal to 280 degrees Fahrenheit.

41. The method of claim 35, wherein the first temperature is room temperature.

42. The method of claim 35, wherein the cooling of the milled item to a cryogenic temperature is a function of detected austenite transition.

* * * * *